(12) United States Patent
Kenany et al.

(10) Patent No.: US 9,040,809 B2
(45) Date of Patent: May 26, 2015

(54) NANO POWER CELL AND METHOD OF USE

(71) Applicants: Saad Al Kenany, Palo Alto, CA (US);
Marc Madou, Palo Alto, CA (US)

(72) Inventors: Saad Al Kenany, Palo Alto, CA (US);
Marc Madou, Palo Alto, CA (US)

(73) Assignee: SOLERA LABORATORIES, INC.,
Sunnyvale, CA (US)

( * ) Notice: Subject to any disclaimer, the term of this
patent is extended or adjusted under 35
U.S.C. 154(b) by 144 days.

(21) Appl. No.: 13/685,635

(22) Filed: Nov. 26, 2012

(65) Prior Publication Data

US 2013/0081672 A1    Apr. 4, 2013

Related U.S. Application Data

(63) Continuation of application No. 12/839,337, filed on Jul. 19, 2010, now Pat. No. 8,319,092, which is a continuation-in-part of application No. 11/934,283, filed on Nov. 2, 2007.

(60) Provisional application No. 60/856,547, filed on Nov. 3, 2006.

(51) Int. Cl.
  *H01G 9/20*    (2006.01)
  *H01L 31/18*    (2006.01)
  *H01L 31/0384*    (2006.01)
  *H01G 9/22*    (2013.01)
  *H01L 31/0352*    (2006.01)

(52) U.S. Cl.
  CPC .......... *H01L 31/0384* (2013.01); *H01G 9/2059* (2013.01); *H01G 9/22* (2013.01); *H01L 31/1892* (2013.01); *A61B 2560/0214* (2013.01); *H01L 31/035218* (2013.01); *H01L 31/18* (2013.01); *Y02B 10/12* (2013.01)

(58) Field of Classification Search
  CPC ........ H01G 9/2059; H01G 9/22; H01L 31/18; H01L 31/1892
  See application file for complete search history.

(56) References Cited

U.S. PATENT DOCUMENTS

| | | |
|---|---|---|
| 4,021,323 A | 5/1977 | Kilby |
| 4,032,477 A | 6/1977 | Gratzel |
| 4,367,131 A | 1/1983 | Gratzel |
| 4,381,978 A | 5/1983 | Gratzel |
| 4,382,846 A | 5/1983 | Gratzel |
| 4,389,290 A | 6/1983 | Gratzel |
| 4,394,293 A | 7/1983 | Gratzel |
| 4,421,617 A | 12/1983 | Gratzel |
| 4,847,231 A | 7/1989 | Gratzel |
| 4,927,721 A | 5/1990 | Gratzel |
| 5,084,365 A | 1/1992 | Gratzel |
| 5,223,634 A | 6/1993 | Gratzel |
| 5,378,628 A | 1/1995 | Gratzel |
| 5,393,903 A | 2/1995 | Gratzel |
| 5,441,827 A | 8/1995 | Gratzel |
| 5,482,570 A | 1/1996 | Saurer |
| 5,728,487 A | 3/1998 | Graetzel |

(Continued)

OTHER PUBLICATIONS

H. Gerisher. "Electrochemical photo and solar cells-principles and some experiments". J. Electroanal. Chem. 58, 263-274 (1975).

(Continued)

*Primary Examiner* — Evan Pert
(74) *Attorney, Agent, or Firm* — DLA Piper LLP (US)

(57) ABSTRACT

A nano power cell and method of use are described wherein the nano power cell absorbs electromagnetic energy is nano particles in an optical fluid that flow in microchannels of the nano power cell.

4 Claims, 14 Drawing Sheets

(56) References Cited

U.S. PATENT DOCUMENTS

| | | | |
|---|---|---|---|
| 5,789,592 | A | 8/1998 | Gratzel |
| 6,024,807 | A | 2/2000 | Pappas |
| 6,067,184 | A | 5/2000 | Bonhote |
| 6,245,988 | B1 | 6/2001 | Gratzel |
| 6,335,480 | B1 | 1/2002 | Bach |
| 6,426,827 | B1 | 7/2002 | Bonhote |
| 6,706,963 | B2 | 3/2004 | Gaudiana |
| 6,734,305 | B2 | 5/2004 | Pierre et al. |
| 6,858,158 | B2 | 2/2005 | Chittibabu |
| 6,900,382 | B2 | 5/2005 | Chittibabu |
| 6,913,713 | B2 | 7/2005 | Chittibabu |
| 6,924,427 | B2 | 8/2005 | Eckert |
| 6,933,436 | B2 | 8/2005 | Shaheen |
| 6,949,400 | B2 | 9/2005 | Ryan |
| 7,022,910 | B2 | 4/2006 | Gaudiana |
| 7,094,441 | B2 | 8/2006 | Chittibabu |
| 7,186,911 | B2 | 3/2007 | Ryan |
| 7,196,834 | B2 | 3/2007 | Brabec |
| 7,205,473 | B2 | 4/2007 | Li |
| 7,220,914 | B2 | 5/2007 | Chittibabu |
| 7,259,324 | B2 | 8/2007 | Zeira |
| 7,304,361 | B2 | 12/2007 | Brabec |
| 7,306,968 | B2 | 12/2007 | Brabec |
| 7,329,709 | B2 | 2/2008 | Gaudiana |
| 7,351,907 | B2 | 4/2008 | Gaudiana |
| 7,407,831 | B2 | 8/2008 | Brabec |
| 7,413,997 | B2 | 8/2008 | Brabec |
| 7,414,188 | B2 | 8/2008 | Gaudiana |
| 7,466,376 | B2 | 12/2008 | Galvin |
| 7,476,278 | B2 | 1/2009 | Brabec |
| 7,522,329 | B2 | 4/2009 | Brabec |
| 7,544,747 | B2 | 6/2009 | Gaudiana |
| 7,994,422 | B2 * | 8/2011 | Jin et al. ................ 136/263 |
| 8,319,092 | B1 | 11/2012 | Kenany et al. |
| 8,574,463 | B2 * | 11/2013 | Tani et al. ............... 252/501.1 |
| 2003/0188776 | A1 | 10/2003 | Li |
| 2003/0188777 | A1 | 10/2003 | Gaudiana |
| 2003/0189402 | A1 | 10/2003 | Gaudiana |
| 2003/0192583 | A1 | 10/2003 | Ryan |
| 2003/0192584 | A1 | 10/2003 | Beckenbaugh |
| 2003/0192585 | A1 | 10/2003 | Beckenbaugh |
| 2004/0025933 | A1 | 2/2004 | Chittibabu |
| 2004/0025934 | A1 | 2/2004 | Chittibabu |
| 2004/0031520 | A1 | 2/2004 | Ryan |
| 2005/0039790 | A1 | 2/2005 | Chittibabu |
| 2005/0040374 | A1 | 2/2005 | Chittibabu |
| 2005/0045851 | A1 | 3/2005 | He |
| 2005/0067006 | A1 | 3/2005 | Eckert |
| 2005/0189014 | A1 | 9/2005 | Gaudiana |
| 2005/0211292 | A1 | 9/2005 | Chittibabu |
| 2005/0279399 | A1 | 12/2005 | Gaudiana |
| 2006/0003217 | A1 | 1/2006 | Cohen et al. |
| 2006/0093017 | A1 | 5/2006 | Gong et al. |
| 2006/0278890 | A1 | 12/2006 | Brabec |
| 2007/0012349 | A1 | 1/2007 | Gaudiana |
| 2007/0089779 | A1 | 4/2007 | Balasubramanian |
| 2007/0102040 | A1 | 5/2007 | Beckenbaugh |
| 2007/0107776 | A1 | 5/2007 | Li et al. |
| 2007/0131277 | A1 | 6/2007 | Gaudiana |
| 2007/0181179 | A1 | 8/2007 | Brabec |
| 2007/0193621 | A1 | 8/2007 | Brabec |
| 2007/0246094 | A1 | 10/2007 | Brabec |
| 2007/0251570 | A1 | 11/2007 | Eckert |
| 2007/0267055 | A1 | 11/2007 | Gaudiana |
| 2007/0289626 | A1 | 12/2007 | Brabec |
| 2007/0295400 | A1 | 12/2007 | Brabec |
| 2008/0006324 | A1 | 1/2008 | Berke |
| 2008/0011352 | A1 | 1/2008 | Zeira |
| 2008/0087324 | A1 | 4/2008 | Gaudiana |
| 2008/0121281 | A1 | 5/2008 | Gaudiana |
| 2009/0050207 | A1 | 2/2009 | Galvin |
| 2010/0218825 | A1 * | 9/2010 | Jee et al. ................ 136/261 |

OTHER PUBLICATIONS

J. Bard. "Photoelectrochemistry". Science 207 [4427], 139-144 (1980).

M. Wrighton. "Photoelectrochemical conversion of optical energy to electricity and fuels". Accounts of Chemical Research 12 [9], 303-310 (1979).

B. O'Regan, M. Grazel. "A low-cost, high-efficiency solar cell based on dye-sensitized colloidal TiO2 films". Nature 353 [6346]: 737-740 (1991).

M. Gratzel. "Dye-sensittized Solar Cells". J. Photochemistry and Photobiology C: Photochemistry Reviews. 4, [2] 145-153 (2003).

M. Grätzel. "Solar Energy Conversion by Dye-Sensitized Photovoltaic Cells". Inorganic Chemistry, 44 [20], 6841-6851 (2005).

Y. Chiba, A. Islam, Y. Watanabe, R. Komiya, N. Koide, L. Han. "Dye-Sensitized Solar Cells with Conversion Efficiency of 11.1%". Jap. J. Appl. Phys. 45, [25] L638-L640 (2006).

T. Tepper, S. Berger. "Correlation between microstructure, particle size, dielectric constant, and electrical resistivity of nano-size amorphous SiO2 powder". Nanostructured Materials, 11 [8], 1081-1089 (1999).

J. Wu, G. Chen, C. Lu, W. Wu, J. "Performance and electron transport properties of TiO2 nanocomposite dye-sensitized solar cells". Nanotechnology 19 (2008).

T. Bruton, G. Luthardt, K. Rasch, K. Roy, I. Dorrity, B. Garrard, L. Teale, J. Alonso, U. Ugalde, K. Declerq, J. Nigs, J. Szlufcik, A. Rauber, W. Wettling, A. Vallera. "A study of the manufacture at 500 MWp p.a. of crystalline silicon photovoltaic modules". Conference Record, 14th European Photovoltaic Solar Energy Conference, Barcelona, pp. 11-16 (1997).

A. Shah, P. Torres, R. Tscharner, N. Wyrsch, H. Keppner. "Photovoltaic Technology: The Case for Thin-Film Solar Cells". Science 30 [285] 692-698 (1999).

X. Wu. "High-efficiency polycrystalline CdTe Thin-film Solar Cells". Solar Energy 77, [6] 803-814 (2004).

N. Naghavi, S. Spiering, M. Powalla, B. Cavana, D. Lincot. "High-efficiency copper indium gallium diselenide (CIGS) solar cells with indium sulfide buffer layers deposited by atomic layer chemical vapor deposition (ALCVD)". Progress in Photovoltaics: Research and Applications 11, [7] 437-443 (2003).

Miasole: Thin Film Solar. Retrieved Jun. 2, 2009, from www.miasole.com.

I. Repins, M. Contreras, B. Egaas, C. DeHart, J. Scharf, C. Perkins, B. To, R. Noufi. "19.9%-efficient ZnO/CdS/CuInGaSe2 solar cell with 81.2% fill factor". Progress in Photovoltaics: Research and Applications 16, [3] 235-239 (2008).

P. Kelly, J. Hisek, Y. Zhou, D. Pilkinton, D. Arnell. "Advanced Coatings through Pulsed Magnetron Sputtering". Surface Engineering 20, [3] 157-162 (2004).

K. Patch. "Solar Cell Doubles As Battery". Technology Review News. (2006).

H. Moor, A. Waldau, J. Herrero, M. Topic, S. Haywood, E. Ozsan, M. Powalla, J. Springer, T. Nicdrig, T. Ricdlc, J. Rath, J. Szlufcik, J. Poortmans, S. Pictruzko, F. Karg, P. Malbranche, B. Dimmler. "European Roadmap for PV R&D". Accessed Feb. 6, 2009. http://paris.fe.uni-lj.si/pvnet/files/PVNET_Roadmap_Dec2002.pdf.

* cited by examiner

US 9,040,809 B2

NANO POWER CELL AND METHOD OF USE

PRIORITY CLAIM

This application is a Continuation of and claims priority under 35 USC 120 to U.S. patent application Ser. No. 12/839,337 filed on Jul. 19, 2010 and entitled "Nano Power Cell and Method of Use" which in turn is a Continuation-in-Part of and claims priority under 35 USC 120 to U.S. patent application Ser. No. 11/934,283, filed on Nov. 2, 2007 and entitled "Nano Power Cell and Method of Use" which in turn claims the benefit under 35 USC 119(e) to U.S. Provisional Patent Application Ser. No. 60/856,547 filed on Nov. 3, 2006 and entitled "Nano Power Cell and Method of Use", the entirety of both are incorporated herein by reference.

FIELD

A nano power cell is described.

BACKGROUND

Solar cells are well known devices that have been developed over a long period of time. For example, FIG. 1 illustrates a liquid junction based dye-sensitized solar cell (DSSC) generated by Michael Gratzel that offers the advantage of high efficiency, manufacturability, and low cost. According to the literature, an efficiency of 11.1% has recently been achieved with such a cell. A typical DSSC cell is composed of a transparent anode made of fluorine-doped tin oxide deposited on a glass substrate, a porous layer of titanium dioxide nanoparticles coated with an absorbing dye (i.e. ruthenium-polypyridine), a metallic cathode, and an electrolyte solution containing a redox couple (e.g., $I^-/I_3^-$) as shown in FIG. 1. These components are relatively simple to assemble and inexpensive compared to silicon based solar cells. The principle of operation of the DSSC is significantly different from that of conventional semiconductor solar cells in which the semiconductor is the source of the photo generated electron/hole pairs and also provides the potential barrier that separates these charges resulting in a photocurrent. In contrast, in the DSSC, the semiconductor is used solely for charge separation and the electron/hole pairs are generated in a separate photosensitive dye attached to the semiconductor. As shown in FIG. 1, the Gratzel solar cell consists of a $TiO_2$ layer forming a nanoporous structure with a dye (e.g., ruthenium-polypyridine) spread throughout its surface. The dye molecules are small and in order to capture a reasonable amount of the incoming light the nanoporous structure is used as a scaffold holding large numbers of the molecules in a 3D matrix, vastly increasing the number of molecules for a given surface area. The charge separation is provided by the semiconductor-liquid junction contact. The $TiO_2$ layer sits on a transparent anode made of fluorine-doped tin oxide ($SnO_2$:F) deposited on the side of the glass plate facing the $TiO_2$ layer.

The electrolyte solution also holds a redox couple (e.g., $I^-/I_3^-$) in the space between the dye coated $TiO_2$ and a cathode, typically a thin film of platinum metal. Photons enter the cell through the transparent $SnO_2$:F window, and, if they have enough energy, they are absorbed by the dye creating an excited dye state with the photoelectron in a higher energy level and a hole left behind in a lower energy state. From this excited state an electron is "injected" into the conduction band of the $TiO_2$. This way the dye molecule is oxidized and would decompose if the hole in the lower energy state didn't quickly react with iodide in the electrolyte oxidizing it to form triiodide (dye regeneration reaction): $3I^- - 2e^- \rightarrow I_3^-$.

The reaction with iodide occurs very quickly compared to the recombination of the injected electron with the oxidized dye molecule, preventing effectively short-circuiting the solar cell. The injected electron then travels to the cathode via the external circuit and the triiodide recovers its missing electron by diffusing through the solution to the cathode where it is reduced back to iodide (redox regeneration reaction): $I_3^- + 2e^- \rightarrow I_3^-$.

Another existing solar cell technology developed by Texas Instrument is shown in FIG. 2. In this approach, electrons and holes are generated in solid junctions inside spherical silicon particles coated with catalytic metals that are in contact with a HBr-containing solution. The reaction of the electrons leads to hydrogen [Redox system 1 $(=H^+/H_2)$] and the reaction of the holes leads to bromine [Redox system 2 $(=Br^-/Br_2)$] and these reaction products are physically separated and coupled to electrodes in a hydrogen/bromide fuel cell. Electrical energy is generated when hydrogen and bromine are allowed to react in the fuel cell and the products of the fuel cell reaction, hydrogen and bromine ions, are brought back to the photoactive cell where they are used again as electrons and holes carriers.

It is desirable to provide a nano power cell that separates the two photo-generated redox pairs while providing a nano power cell and it is to this end that the disclosure is directed.

DETAILED DESCRIPTION OF ONE OR MORE EMBODIMENTS

A nano power cell is described that has a channel and that uses nano particles and an optical fluid flowing in the channel (s) to absorb electromagnetic radiation, such as infrared or visible radiation, and generate energy that can be used to power various devices. In one example of the use of the nano power cell below, the nano power cell may be used to power a medical device and it is in this context that the nano power cell is described. However, the nano power cell may be used to power other devices, such as cellular/mobile phone in which solar and/or infrared energy is used to generate the power. The nano power cell may be to power any other device that needs electrical power to operate, such as iPods, MP3 players, night vision goggles, handheld devices and the like. In other embodiments, the nano power cell may generate energy from infrared radiation, solar/visible light radiation or both solar and infrared radiation wherein the nano power cell may include infrared and solar/visible radiation sensitive nano particles. The nano power cell can also be used for any other device in which it is desirable to provide power for the device. In addition, the nano power cell may further include a power storage unit that may be attached or integrated with the nano power cell. In addition, the heat generated by the device, such as the cellular/mobile phone, computer, etc. which is powered by the nano power cell may be fed back to the nano power cell so that the nano power cell can generate some power from the heat generated by the device. Now, an example of the use of the nano power cell to power an implanted medical device is described in more detail.

Figure 3:
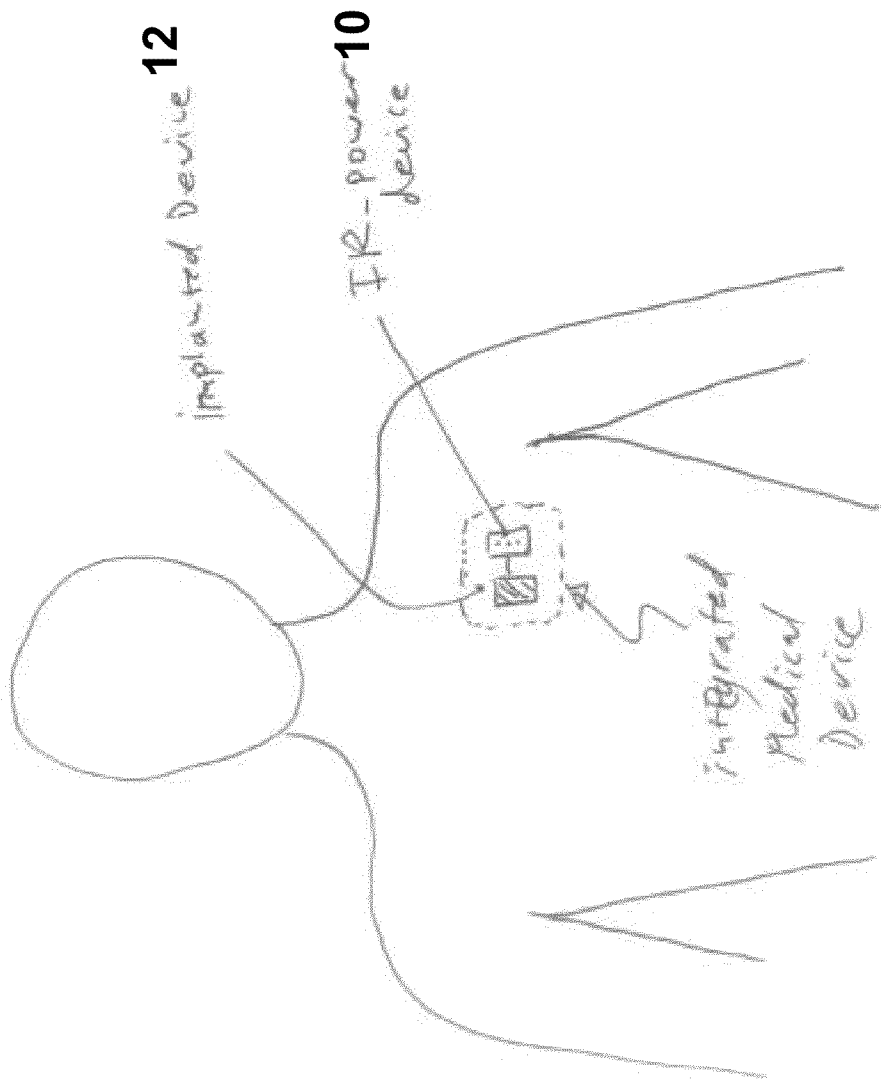
FIG. 3 illustrates an example of the use of a nano power cell.

FIG. 3 illustrates an example of the use of a nano power cell 10 wherein the power cell is powered by infrared energy such as the heat generated by a human body. Thus, the power cell 10 can be coupled to a medical device 12 to form an integrated medical device 14. The power cell, using the infrared energy (heat) of the human body in which the integrated medical device is implanted, generates power that is used to power the medical device. Thus, the integrated medical device 14 does not require an external power source nor an implanted power source that must be periodically removed from the human body and replaced when the power source is exhausted. This use of the nano power cell 10 is merely an example of the use of the power cell since it can be used with any device in which it is desirable to be able to provide power to the device using a power cell that generates energy from any type of electromagnetic energy, such as infrared energy, visible solar energy and the like.

Figure 4:
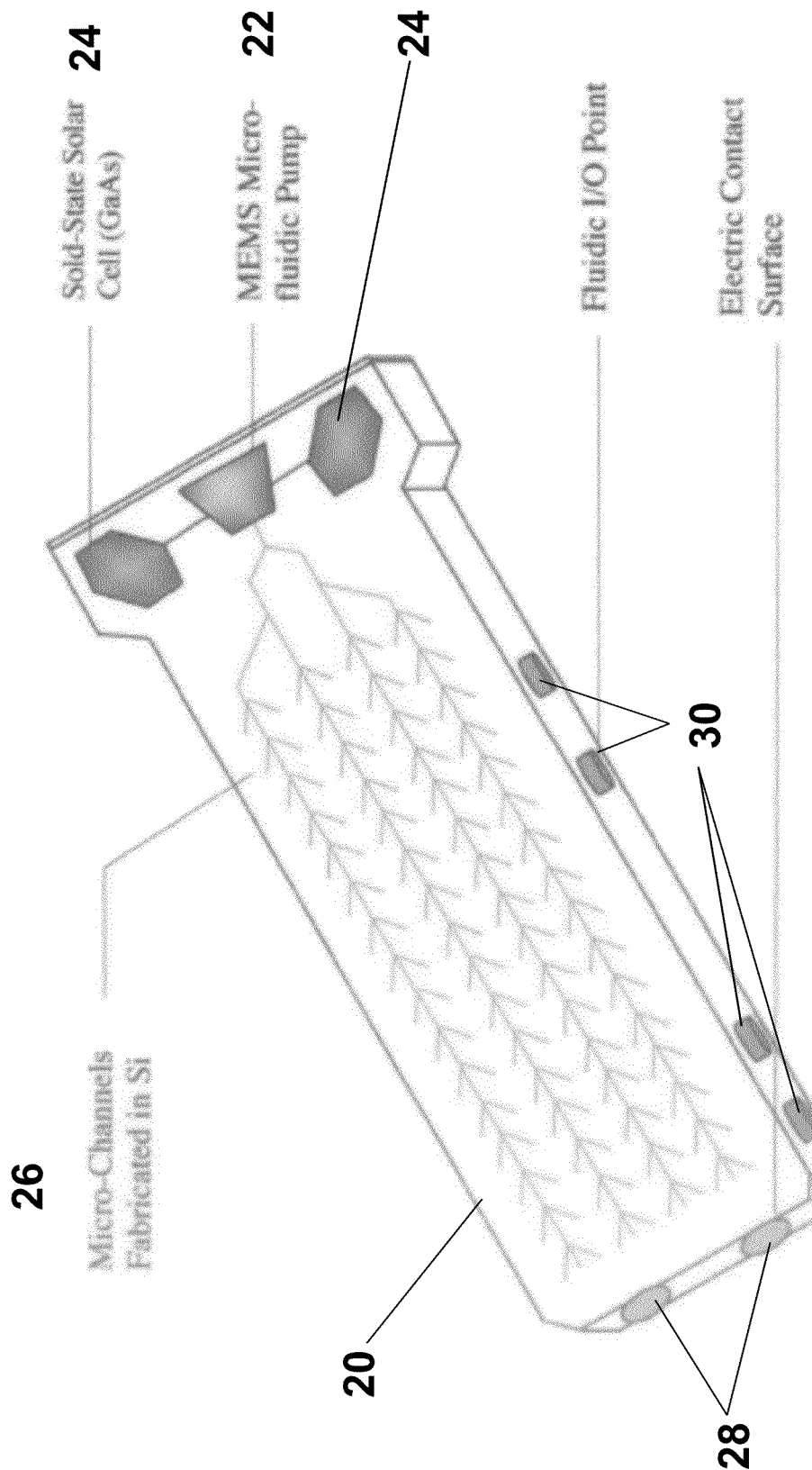
FIG. 4 illustrates an embodiment of a nano power cell.
Figure 5:
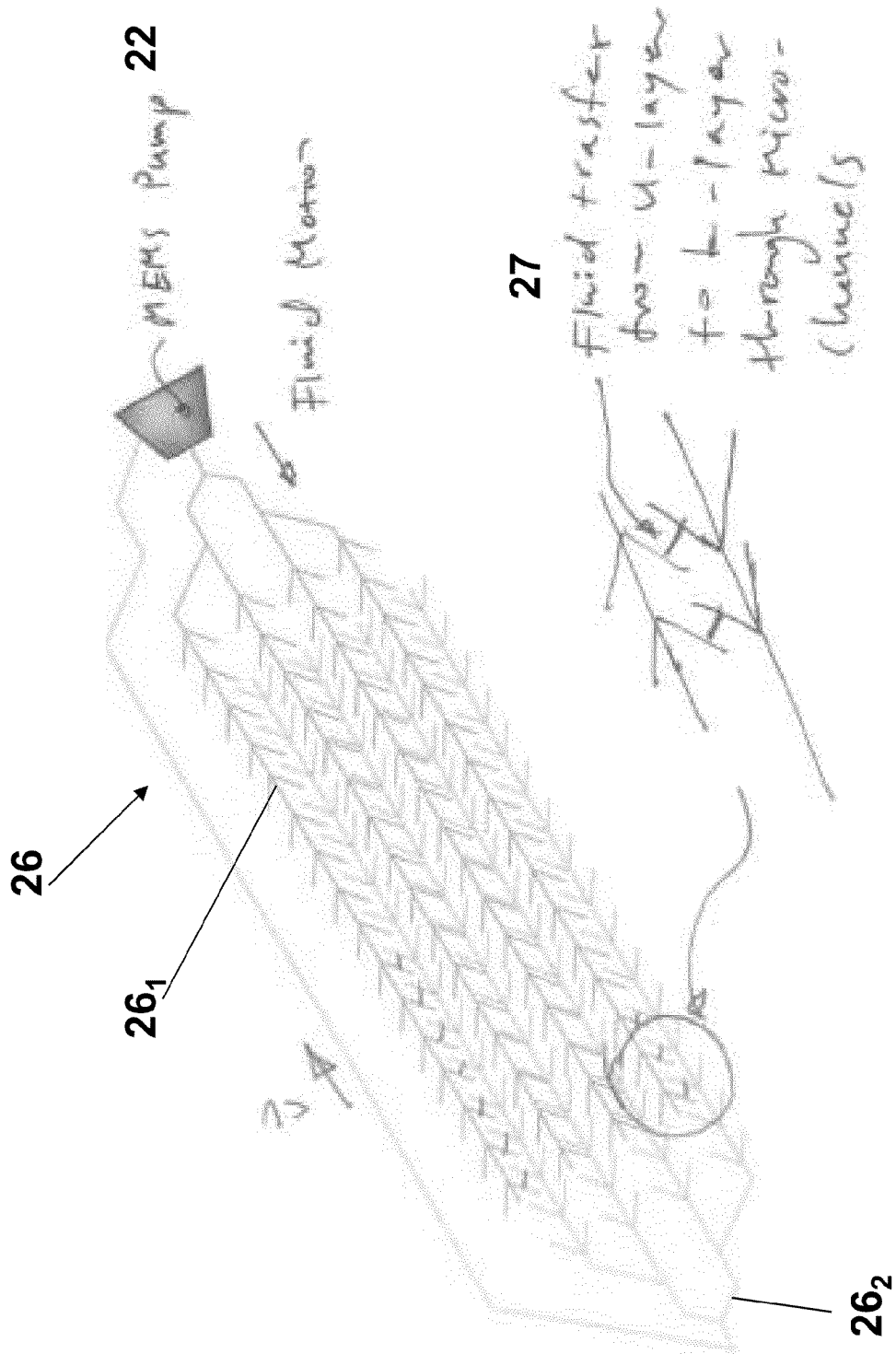
FIGS. 5 and 6 illustrate further details of the nano power cell.

FIG. 4 illustrates an embodiment of a nano power cell 10. The cell may include a substrate/housing 20, that may be made of silicon is one embodiment, that may be multi-layered. The housing 20 may house a micro-electro-mechanical systems (MEMS) nano pump 22 that is coupled to one or more energy generation cells 24, such as infrared sensitive cells made of Gallium Arsenide (GaAs) that provides initial start-up power to the pump 22. In an embodiment in which the nano power cell is used with a device that is not implanted into a human being, the energy generation cells 24 may be solar cells or other cells that are capable of generating the initial start-up power for the pump 22. The pump 22 may further be coupled to one or more sets of microchannels 26 that are formed in the housing such as by fabricating the microchannels in the silicon using a well known process. In one exemplary embodiment, there may be an upper microchannel level and a lower microchannel level as shown in FIG. 5 which will be described below in more detail. The pump 22 may circulate a fluid, such as an optical fluid that may be commercially available LS-5238, through the microchannels and back to the pump wherein the fluid may be a fluid with nano-sized particles in the fluid that are sensitive to the electromagnetic radiation, such as infrared, that strikes the nano particles in the microchannels. In one embodiment, the particles may be Gallium Arsenide (GaAs), Germanium (Ge), Indium Gallium Arsenide (InGaAs) and/or Indium Phosphide (InP). In operation, the fluid with the nano-sized particles circulates through the microchannels and, during that circulation, the particles absorb energy from the electromagnetic energy generated by the body wherein the energy is stored as an electrical charge in the particle. The speed/velocity of the fluid flowing through the microchannels is such that the particles each receive the optimal amount of energy while exposed to the electromagnetic energy. The optimal amount of energy is as much energy as each particle is able to store without overcharging the particles or having the particles exposed to the electromagnetic energy when the particle is already fully charged. The electrical charge on each particle is then transferred to an electrode in the power cell which may store the accumulated electrical charge.

Figure 1:
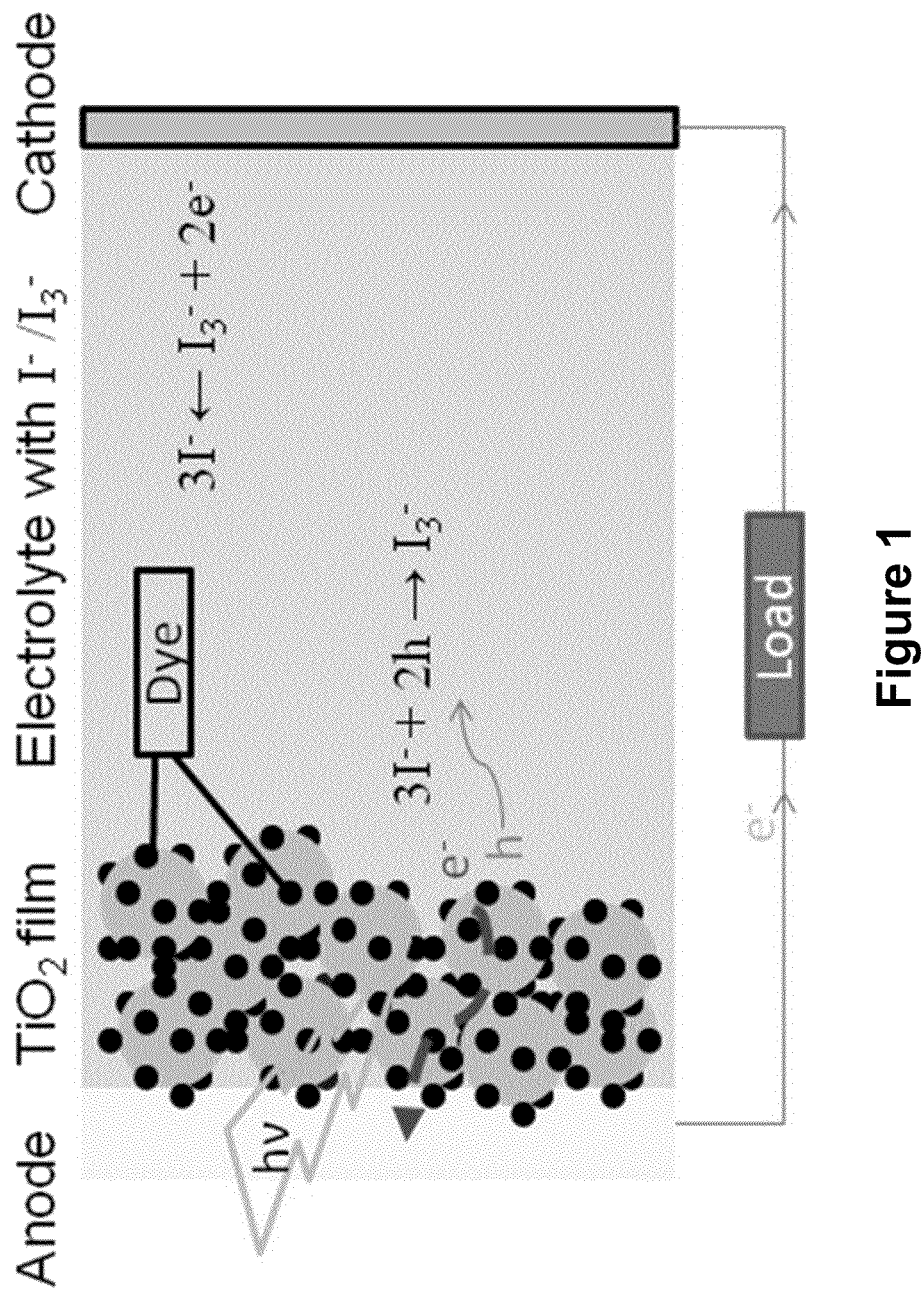
FIG. 1 illustrates a dye-sensitized Grätzel design liquid-junction solar cell.
Figure 2:
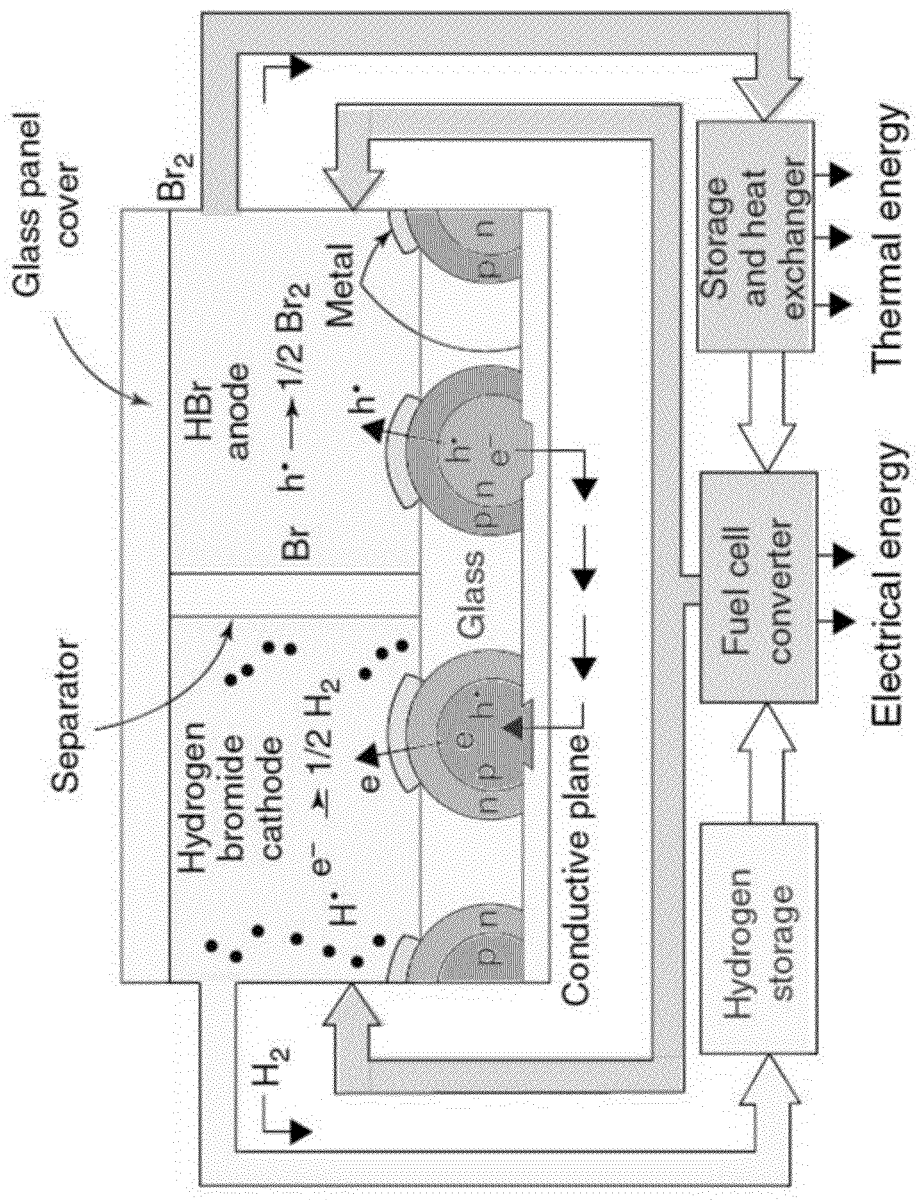
FIG. 2 is a schematic drawing of a solar cell made by Texas Instruments.

Returning to FIG. 4, the power cell 10 may further comprise a set of electrical contacts 28 wherein the electrical energy from the power cell is output from the power cell 10 to a device, such as the implanted medical device 12 shown in FIG. 1. The power cell 10 may further comprise one or more fluidic input/output ports 30 that permit the fluid with the nanoparticles to be added or removed from the power cell. Because microchannels are used in the power cell, there is a larger surface area of the microchannels which in turn means that there is more exposure of the particles to the electromagnetic radiation. In addition, the nanoparticles have a larger surface area that a larger particle occupying the same volume that further increases the amount of absorption of the electromagnetic energy by the power cell. In addition, the flow of the particles in the fluid results in the constant charge and discharge of the electromagnetic energy carrying particles so that a charge/recharge cycle typical with cells with fixed energy absorption cells in not required. In order words, the power cell 10 does not have a typical discharge time associated with it during which the user must wait for the fixed cells to be discharged before recharging the cell. The particles in the fluid are also exposed to radiation on all sides of the particle since the orientation of the particle to the radiation source in the fluid is not fixed and changes constantly. Thus, the power cell 10 has a higher efficiency than typical power cells.

Figure 6:
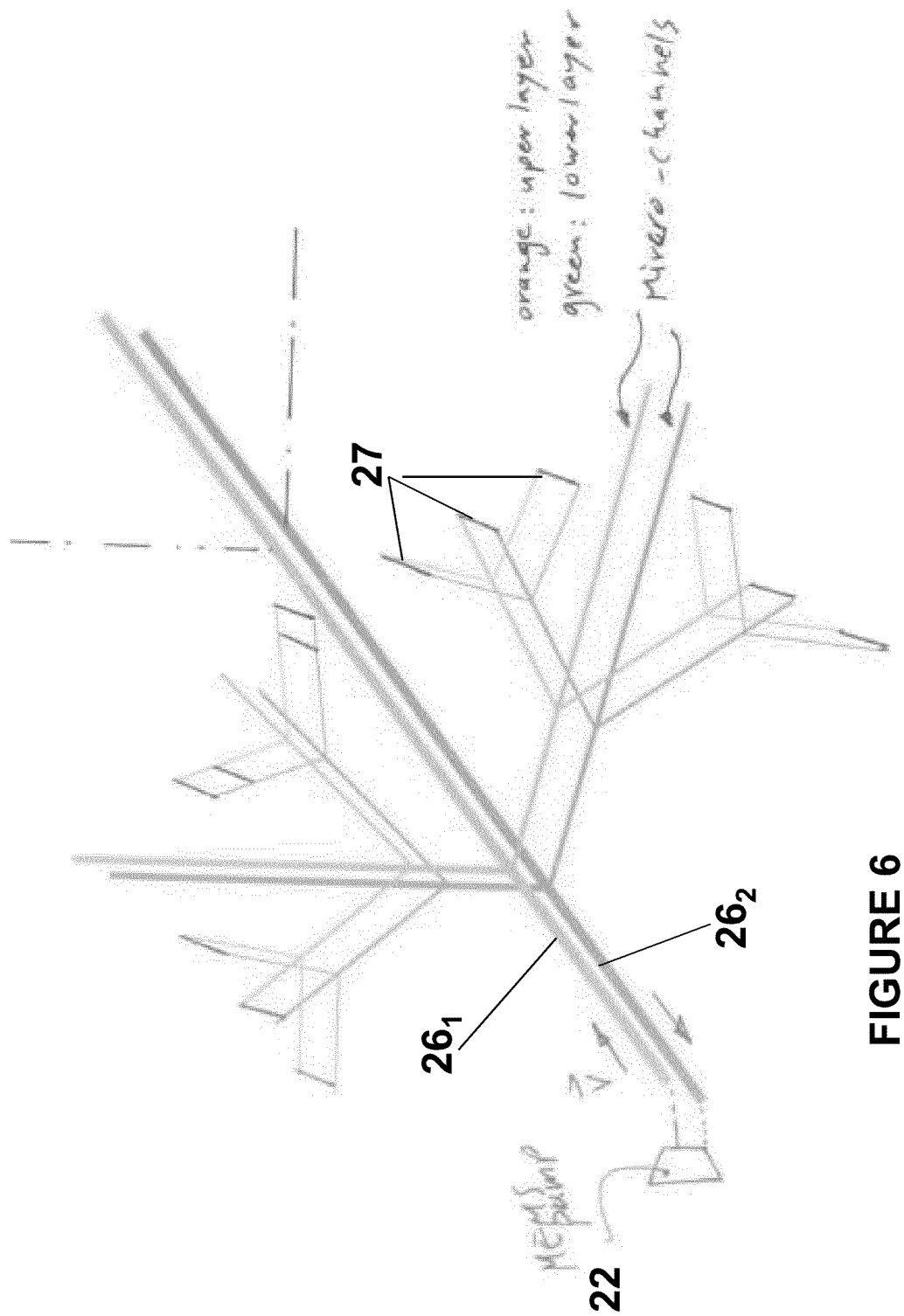

FIGS. 5 and 6 illustrate further details of the nano power cell. In particular, FIGS. 5 and 6 illustrate the microchannels 26 coupled to the pump 22 and in particular an upper level microchannel $26_1$ and a lower level microchannel $26_2$ that are vertically displaced from each other within the housing. As the fluid circulates through the microchannels (with the flow being away from the pump 22 through the upper level microchannels $26_1$ and then back to the pump through the lower level microchannels $26_2$) the fluid passes from the upper level microchannels to the lower level microchannels via capillaries 27 that connect the two microchannels at the end branches of the microchannels.

Figure 7:
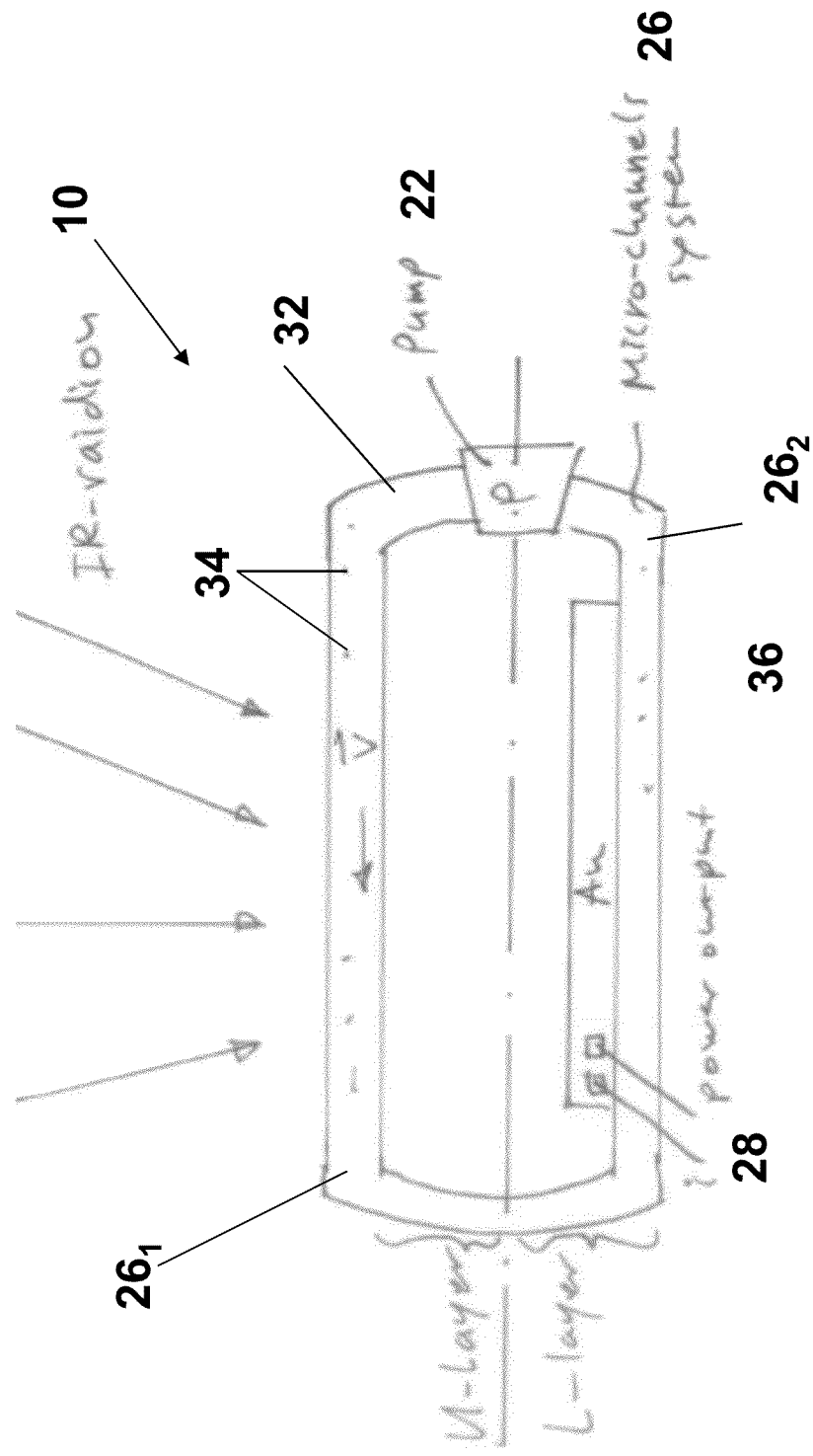
FIG. 7 illustrates a cutaway side view of the nano power cell shown in FIG. 3.

FIG. 7 illustrates a cutaway side view of the nano power cell 10 shown in FIG. 1 wherein the upper microchannels $26_1$ and the lower microchannels $26_2$ are shown connected to the pump 22 and connected to each other to form a fluid flow path. A fluid 32, such as an optical fluid, with nanoparticles 34 flow out from the pump through the upper microchannels $26_1$ and the back to the pump through the lower microchannels $26_2$. The nanoparticles may be 1 nanometer to 10 micrometers in size. The pump 22 generates a fluid velocity ($\vec{v}$) and therefore a particle velocity that is optimized to have a maximum charge absorbed by each particle in a minimum amount of time and then fully discharge the particles as described below. In particular, the velocity is optimized so that the particles spend just enough time in the upper microchannels $26_1$ exposed to the electromagnetic radiation in order to acquire a maximum charge without becoming overcharged. Once the particles are charged while traveling in the upper microchannels $26_1$, they transition into the lower microchannels $26_2$ where they come into contact with an plate 36, such as a gold plated silicon plate/electrode) where the particles discharge their charge onto the plate. As described above, the velocity ($\vec{v}$) of the fluid is optimized to permit the particles to full discharge in a minimum amount of time. The specific velocity ($\vec{v}$) for any particular nano power cell will depend on the fluid and particles used, the size of the microchannels, the type of electromagnetic radiation and the sensitivity of the nano particles to the particular type of electromagnetic radiation and the size of the plate and could be calculated by one of ordinary skill in the art.

Figure 8:
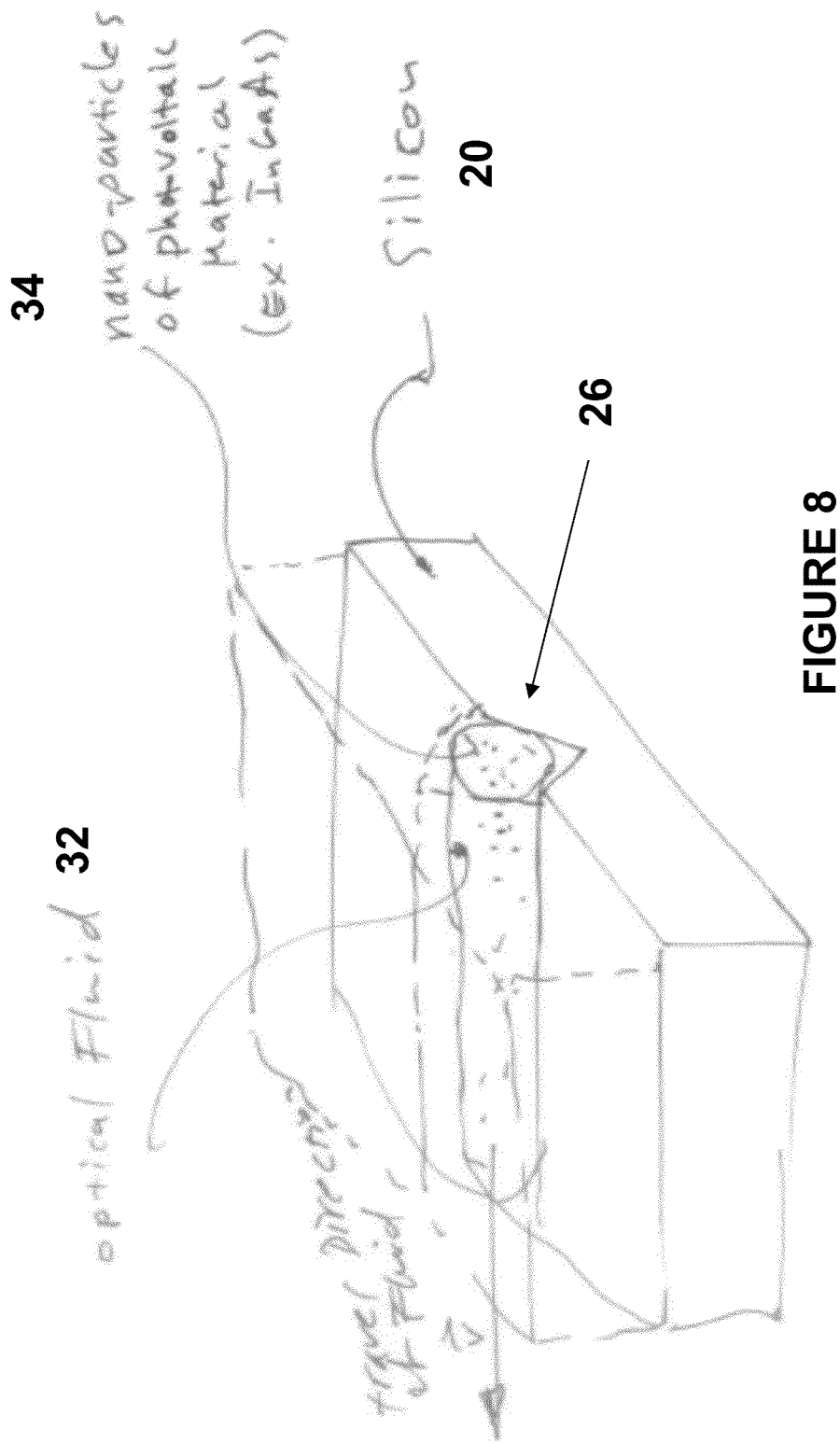
FIG. 8 illustrates a micro-channel that contains a fluid with nano-particles.

FIG. 8 illustrates a micro-channel 26 in the housing 20 that contains the fluid 32 with the plurality of nano-particles 34 that flow with a velocity ($\vec{v}$) within the fluid that is within the microchannel. The nano particles in the fluid in the microchannels result in a better energy absorption efficiency that other electromagnetic energy absorbing devices for various reasons. First, the microchannels have more surface area than typical channels and therefore expose more particles to the electromagnetic energy. Second, the nanoparticles, for a particle volume, have a larger surface area than a larger particle occupying the same volume as is well known. Third, the particles in the fluid are being constantly charged and discharged due to the fluid flow so they have a shorter charge/discharge cycle time that a fixed particle device. Fourth, since the particles rotate and move in the fluid, more of the surface area of each particle is exposed to the electromagnetic energy than with a fixed particle.

In another embodiment, the fluid may have infrared sensitive particles and visible sensitive particles mixed together so that the nano power cell can generate energy from the infrared energy as well as the visible electromagnetic energy during the circulation of the fluid in the nano power cell.

Figure 9:
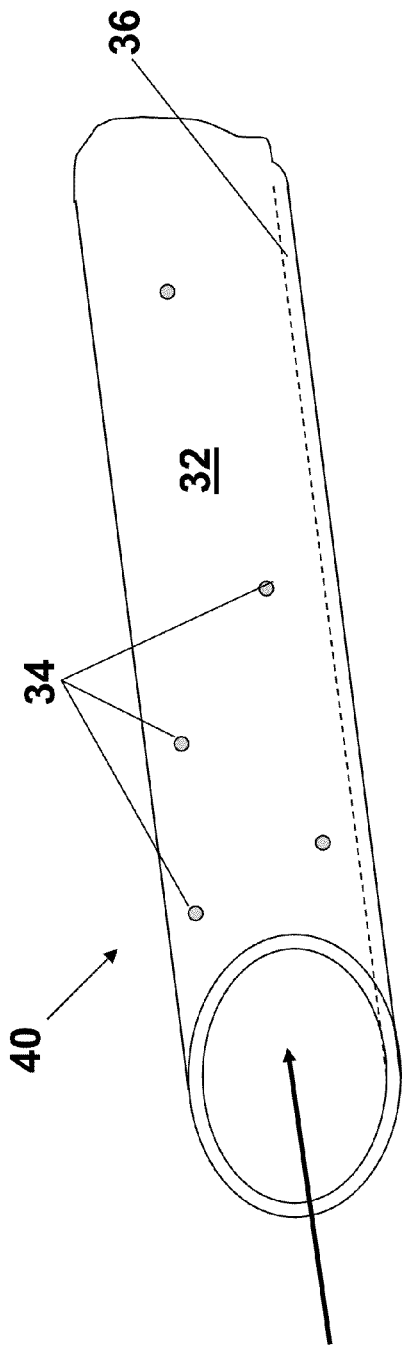
FIGS. 9-11 illustrate another embodiment of the nano power cell.
Figure 10:
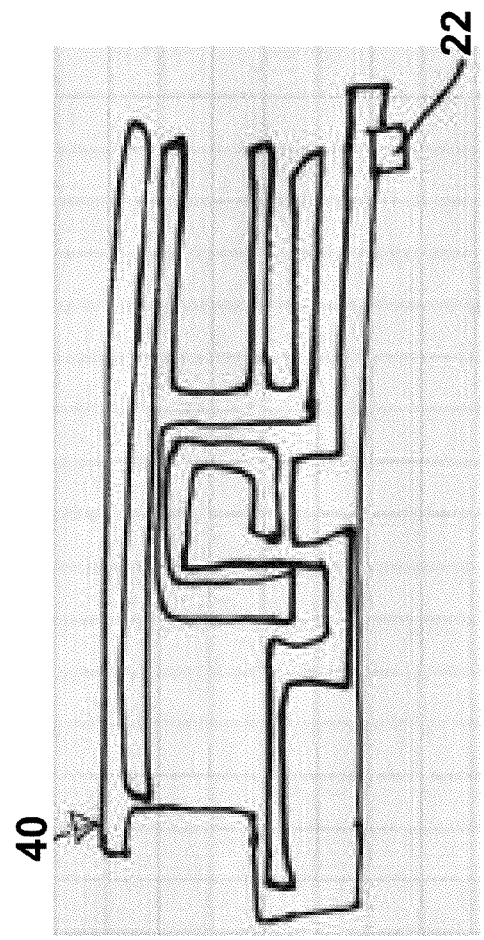
Figure 11:
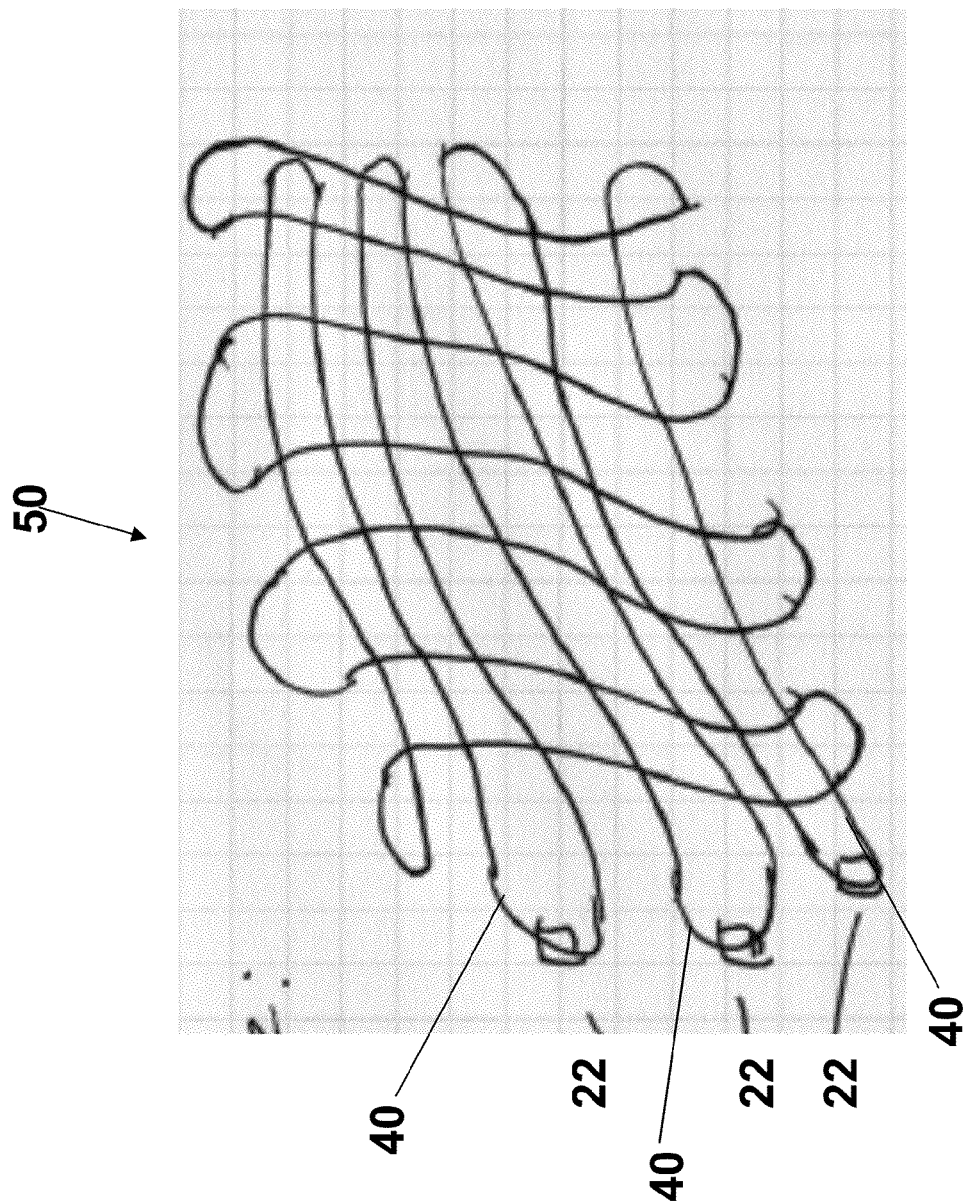

FIGS. 9-11 illustrate another embodiment of the nano power cell in the form of a fiber 40 or a thin transparent pipe (up to 125 microns) such an optical fiber that has an interior channel as shown in FIG. 9. The fiber 40 has the fluid 32, such as an optical fluid or a Photo-Voltaic-Nano-Materials (PVNM)-saturated optical fluid, with the nanoparticles 34 that flows through the fiber and contact a plate 36 (or a metallic coating inside of the hollow fiber or the thin transparent pipe) that is located inside that allows the nanoparticles to absorb energy and then discharge that energy to the plate as described above. FIG. 10 illustrates an example of a fiber with a particular exemplary pattern and the pump 22 that pumps the fluid with the nanoparticles through the fiber. The fiber as shown in FIGS. 10 and 11 may be used to make a fabric (as shown in FIG. 9) that creates flexible power generating structures in large areas that can be applied in any surface. As shown in FIG. 9, a piece of fabric 50 made with one or more fibers 40 may have one or more pumps 22 that circulate the fluid through the fibers 40. Thus, the entire piece of fabric becomes an energy generation device/system that can be made so that it covers a large surface area and generates energy from the electromagnetic radiation. Using the fiber shown in FIGS. 7-8, other devices/structures may also be formed that are made of or contain the fibers such as buildings, roofing shingles, the external surfaces of products and the like.

Figure 12:
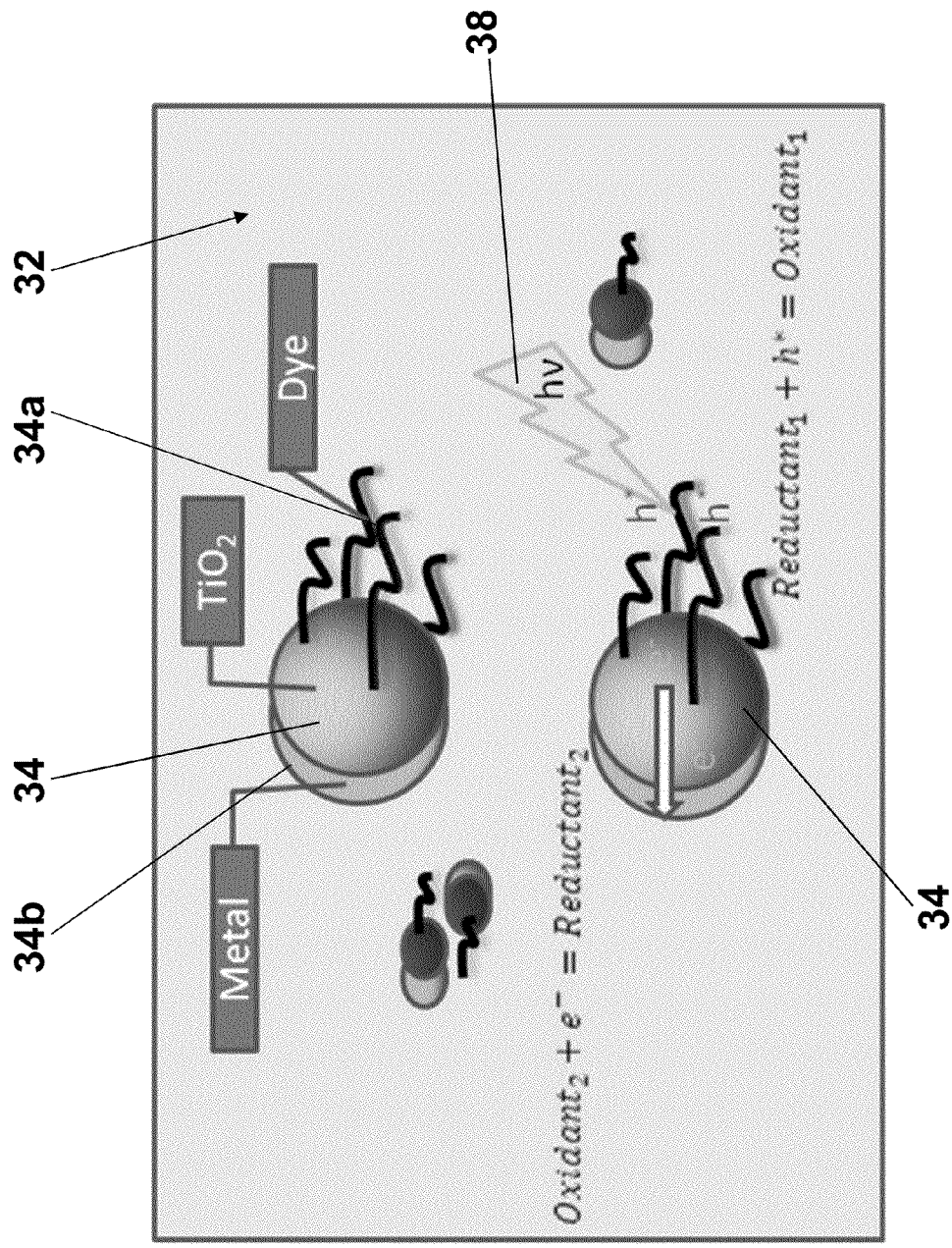
FIG. 12 illustrates the optical fluid and nanoparticles for a second embodiment of the nano power cell.

FIG. 12 illustrates the optical fluid 32 with the nanoparticles 34 for a second embodiment of the nano power cell in which the nanoparticles are dispersed three dimensional particles. The particles may be $TiO_2$ or $ZnO$ particles. In addition, the nano power cell may use both nano sized particles (from 1 nanometer to 20 nanometers) and micro sized particles (from 0.1 micrometers to 100 micrometers) together in the liquid 32 so that a wide range of the electromagnetic spectrum can be captured by the particles. More generally, the nano power cell may use any stable electrochemical particles and, in particular, any stable semiconductor particles. For example, in addition to the examples above ($TiO_2$ or $ZnO$), the nano power cell may use any of the different particles identified in the following references: O'Regan, M. Gratzel. "A low-cost, high-efficiency solar cell based on dye-sensitized colloidal TiO2 films". Nature 353 [6346]: 737-740 (1991); M. Gratzel. "Dye-sensittized Solar Cells". J. Photochemistry and Photobiology C: Photochemistry Reviews. 4, [2] 145-153 (2003); M. Gratzel. "Solar Energy Conversion by Dye-Sensitized Photovoltaic Cells". Inorganic Chemistry, 44 [20], 6841-6851 (2005); U.S. Pat. No. 6,734,305; U.S. Pat. No. 6,426,827, U.S. Pat. No. 6,335,480; U.S. Pat. No. 6,245,988; U.S. Pat. No. 6,067,184; U.S. Pat. No. 6,024,807; U.S. Pat. No. 5,789,592; U.S. Pat. No. 5,728,487; U.S. Pat. No. 5,482,570; U.S. Pat. No. 5,441,827; U.S. Pat. No. 5,393,903; U.S. Pat. No. 5,378,628; U.S. Pat. No. 5,223,634; U.S. Pat. No. 5,084,365; U.S. Pat. No. 4,927,721; U.S. Pat. No. 4,847,231; U.S. Pat. No. 4,421,617; U.S. Pat. No. 4,394,293; U.S. Pat. No. 4,389,290; U.S. Pat. No. 4,382,846; U.S. Pat. No. 4,381,978; U.S. Pat. No. 4,367,131 and U.S. Pat. No. 4,032,477, all of which are incorporated herein by reference As shown in FIG. 12, each nanoparticle may be coated with (or otherwise have the two portions affixed to the nanoparticle) a dye portion 34a and a metallic portion 34b wherein the two portions may be on respective first and second surfaces of the particle. The dye portion and the metal portion are the anode and cathode, respectively for each particle. When different sized particles exist in the liquid 32, several different dye sensitizers may be used to further enhance the ability to capture energy from a wider range of the electromagnetic spectrum.

The nanoparticles are then suspended in the liquid 34. The liquid 32 may contain a first oxidant ($oxidant_1$), a second oxidant ($oxidant_2$), a first reductant ($reductant_1$) and a second reductant ($reductant_2$) that form two non-recombining redox systems which may be separated from each other to prevent re-combination of the electrons as described below in more detail. Thus, the electrical contact and energy transfer between the particles 34 and two electrodes in an in-situ energy storage compartment are made via two redox systems suspended in a fluidic system. The metals that can be used with the system include any electocatalytic metals that do not dissolve or corrode in a solution. The dyes that can be used with the system include any photochemical stable dye that absorbs any spectrum of electromagnetic energy. The oxidants and reductants that can be used with the system include any oxidant/reductant pair with the biggest possible redox potential difference. For example, the oxidant/reductant pairs may be an oxidant/reductant pair in which the voltage differential between the two is maximized and/or the lipophilic and hydrophilic with opposite soluability and/or two pairs with different sedimentation rates. As one example, the oxidant/reductant pair may be iodide and iodine. The two redox system equations are:

$$oxidant_2 + e^- = reductant_2 \quad (1)$$

and $$reductant_1 + h^{*-} = oxidant_1 \quad (2)$$

In operation, sunlight (in the form of one or more photons 38—hv as shown in FIG. 12) enters the nano power cell and impinges on the dye portion 34a on the surface of the particle 34. The photons striking the dye with enough energy to be absorbed will create an excited state of the dye, from which an electron (e⁻) can be "injected" directly into the conduction band of the particle 34. The electron moves towards the metal portion 34b of the particle and oxidant$_2$ combines with the electron to form reductant$_2$. The creation of the electron also creates a hole (h*) moves towards the dye portion 34a of the particle and combines with the first reductant to form the first oxidant as shown. The overall reaction with the nano power cell is described in more detail below with reference to FIG. 15.

Returning to FIG. 12, the generation of electron-hole pairs in free photoactive particles and the associated redox reactions occurring on their surfaces are more easily maximized when a larger fraction of all particles have the potential to be photo excited and are freely surrounded by the redox systems with which the electron/hole pairs generated in these particles have to react. Thus, unlike the compressed powders of the $TiO_2$ films in Gratzel cells in which the rate of electron regeneration is limited by the electrolyte diffusivity, singulated 3D photoactive particles in a solution are in direct contact with the redox pairs and the exchange of charges is almost instantaneous. Furthermore, by employing a flow system due to the pump 22 and channels 26 as shown in FIG. 7, the reaction rates of electrons and holes with the redox systems in solution can be further enhanced, since unlike in the case of a porous planar film, convection can increase the redox pairs transport rates.

The semiconductor micro or nanoparticles in the energy cell each feature their own local anode and cathode as shown in FIG. 12 and are contacting a liquid. The electrical contact and energy transfer between the solar particles and two electrodes in an in-situ storage compartment are made via two redox systems suspended in the fluidic system that is described below in more detail.

Figure 13:
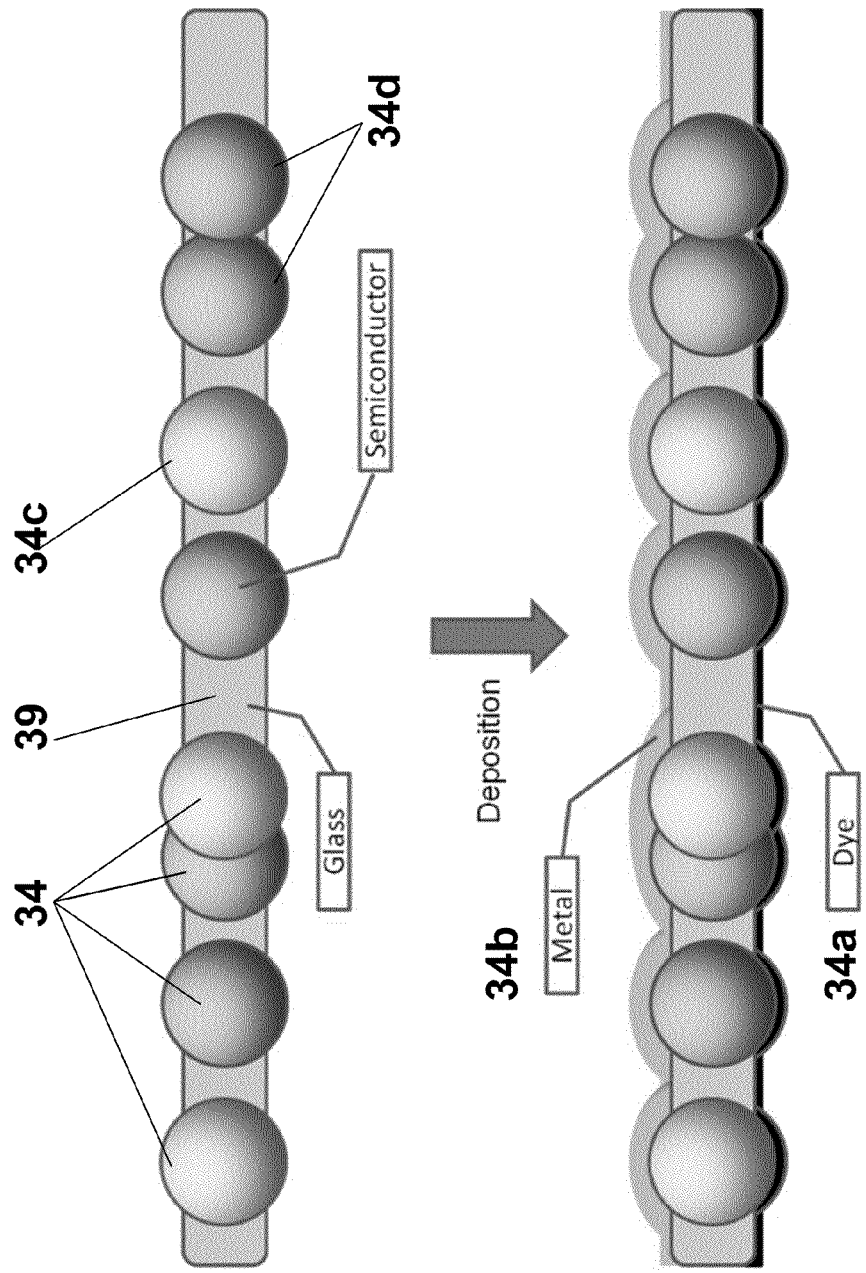
FIG. 13 illustrates particles embedded in a separation barrier of the second embodiment of nano power cell.
Figure 15:
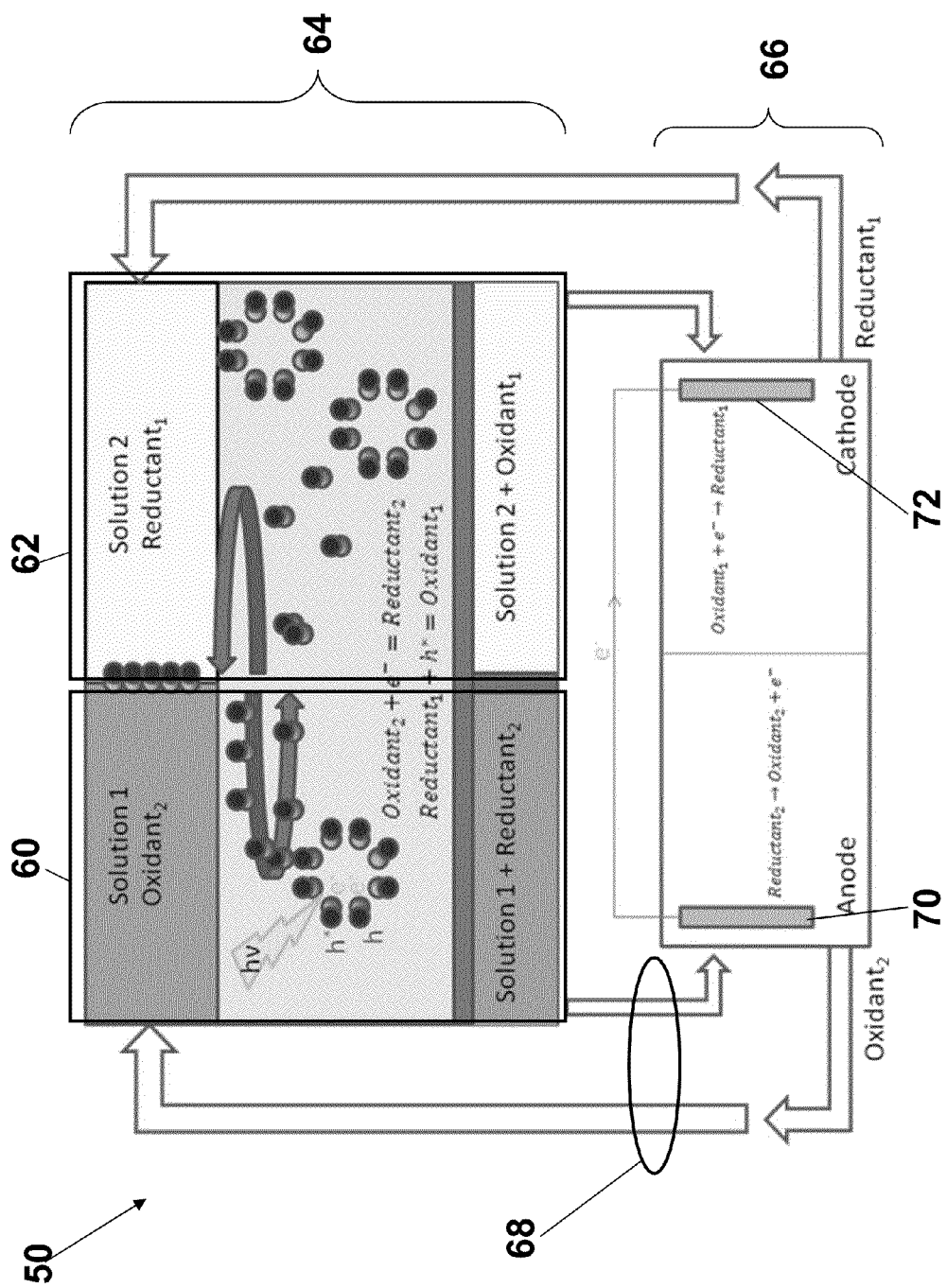
FIG. 15 is a schematic diagram of the second embodiment of the nano power cell that is a three dimensional photoelectrochemical solar cell with dye sensitization.

In the energy cell, it is necessary to prevent the recombination of the two redox pairs before the two redox pairs reach the storage compartment. One technique is a physical barrier that can prevent the recombination of the two redox pairs before the two redox pairs reach the storage compartment. Alternatively, the property differentials between the redox pairs may also be used to prevent the recombination of the two redox pairs before the two redox pairs reach the storage compartment. For example, a physical barrier that keeps redox pairs apart may be used such as shown in FIG. 13 in which the particles are embedded in a transparent polymer or glass sheet separating the anodes and cathodes. As another example, the two redox pairs can be distributed between two non-mixing liquids as shown in FIG. 15 which is described in more detail below. As another example, the two redox pairs may have different property characteristics (such as different solubility, different densities and/or different volatilities, etc. that prevent the recombination of the two redox pairs) in the same liquid to prevent the recombination of the two redox pairs before the two redox pairs reach the storage compartment. Now, a first example of the separation of the redox pairs is described in more detail.

FIG. 13 illustrates particles 34 embedded in a separation barrier of the nano power cell. In particular, the two redox pairs are separated by a physical barrier. An example physical barrier with relatively large embedded semiconductor particles (10-250 µm) is shown in FIG. 13 in which the particles 34 are embedded in a sheet 39.

In a possible fabrication sequence of such sheets, the particles 34 are embedded in a sheet, that may be glass in one example, and the sheet is etched back to reveal a top portion 34c and a bottom portion 34d of the embedded particles 34. Then, on one side of the sheet, the particles 34 are covered, using a conventional deposition process, with a metal 34b, such as a catalyst (e.g., platinum, etc.) On the other side of the sheet, an organic dye 34a is allowed to attach itself on to the exposed particles. The end result is an array of particles embedded in a thin separator film coated with dye on one side and a metal. Thus, the two redox pairs are separated to prevent the recombination of the two redox pairs before the two redox pairs reach the storage compartment.

Figure 14:
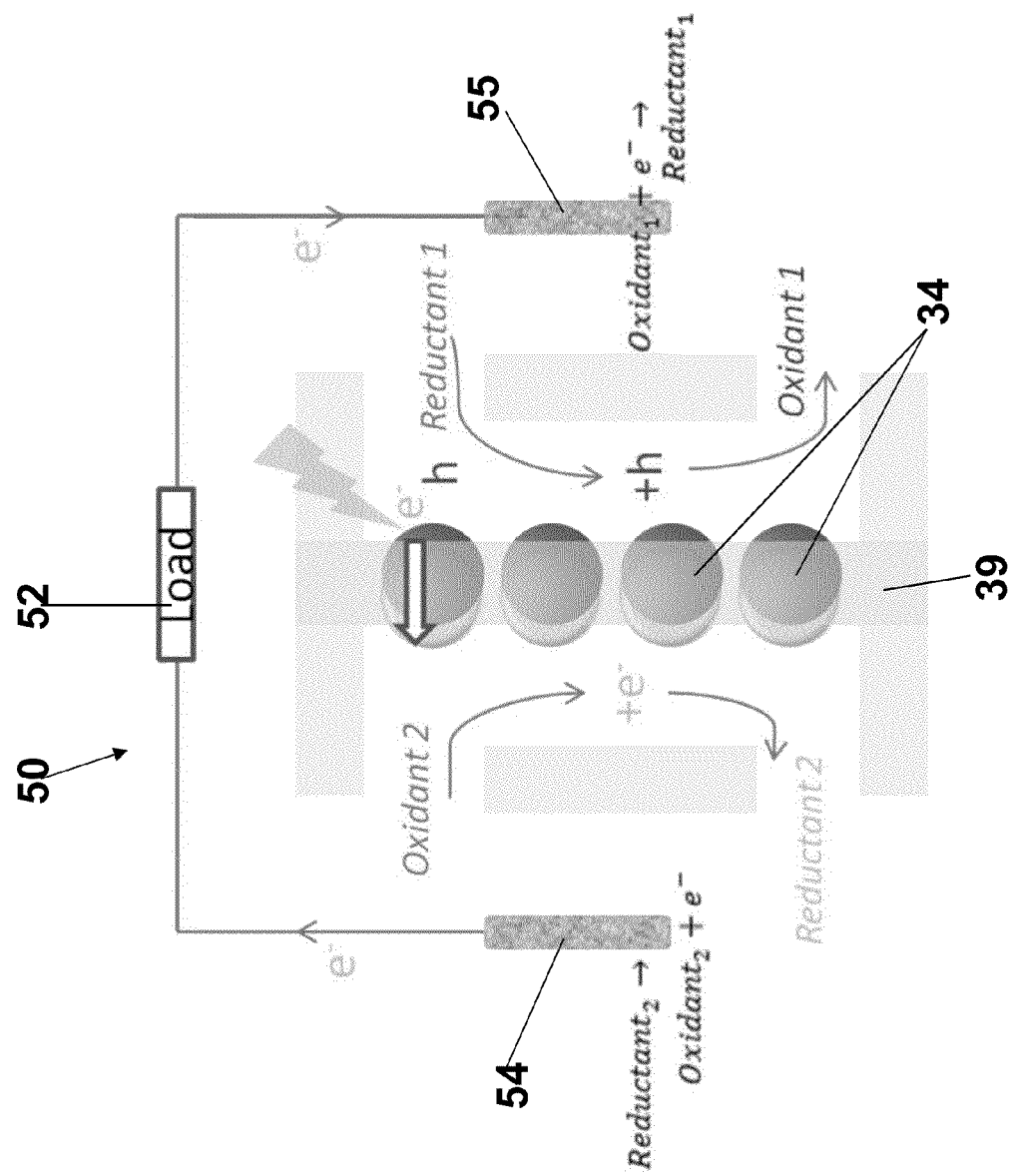
FIG. 14 is a schematic diagram of the physical barrier separating the redox pairs of the second embodiment of the nano power cell.

FIG. 14 is a schematic diagram of the physical barrier 39 shown in FIG. 13 being used to separate the redox pairs of the nano power cell 50. In the power cell 50, the barrier 39 is then placed between two solutions holding the separated redox pairs (oxidant 2, electrons and reductant 2 along with oxidant 1, holes and reductant 1.) Since the redox pairs are physically completely separated in this example, water can be used on both sides of the separator. This example of the nano power cell also has an anode and cathode 54, 55 as shown. In operation, a flow system directs Oxidant 2 and Reductant 1 back into the photoactive cell where the cycle is repeated to generate energy that can be used for a load 52. Now, another embodiment of the power cell is described.

FIG. 15 is a schematic diagram of another embodiment of the nano power cell 50 that is a three dimensional photoelectrochemical solar cell with dye sensitization in which the separation of the redox pairs relies on their distribution between two non-mixing liquids 60, 62 For example, two non-mixing liquids may be oil and water. In addition, other exemplary non-mixing liquids are two liquids in which the different oxidant or reductant dissolve in each different liquid or the liquids may be chemically synthesized. In addition, the liquids may be liquids wherein the first liquid is oxidant$_2$ and the second liquid is reductant$_1$. As can be seen in FIG. 15, the particles in this case are required to be amphipolar in order to preferentially align at the interface between these two solutions. Mixing via chaotic advection creates stretching and folding of the interface boundary effectively increasing the surface area for the electron and hole to be coupled with their respective redox species. After mixing, the two solutions separate back out due to their polarity differences and a potential difference is established between these two solutions.

This nano power cell has a reaction chamber portion 64 and a fuel cell portion 66 that are fluidly connected to each other by a fluidic system 68. The reaction chamber portion 64 is exposed to electromagnetic radiation so that the reaction described above can occur. The fuel cell portion 66 is not exposed to electromagnetic radiation so that the generated holes and electrons can be captured to form an electrical energy. The fuel cell 66 has an anode 70 and cathode 72 as shown.

In operation, the redox systems operate in the reaction chamber portion 64 to form oxidant$_1$ and reductant$_2$ using the same equations described above. Reductant$_2$ is circulated, using the fluidic system, to the anode 70 of the fuel cell where reductant$_2$→oxidant$_2$+e⁻ while oxidant$_1$ is circulated to the cathode 72 of the fuel cell where oxidant$_1$+e⁻→reductant$_1$ so that electrical energy is generated. The reaction products of the fuel cell (oxidant$_2$ and reductant$_1$) can again be directed by the fluidic system 68 back into the photoactive cell (the reaction chamber portion) where the cycle is repeated as shown in FIG. 15. As with the previous examples, the reaction chamber portion 64 may be implemented as described above with microfluidic pumps, micro-channels and the nano-particles suspended in a fluid.

In addition to the example in FIG. 15, the nano power cell can also use other separation mechanisms that rely on the property differences between two redox pairs, including differences in buoyancy, etc as described above so that the nano power cell can be implemented with any of these different separation mechanisms.

The nano power cell as described above has non-recombining redox pairs technology that allows for the production of three dimensional electromagnetic energy cells that maximize electromagnetic energy gathering efficiency. The nano power cell should allow the dramatic reduction of solar cell production cost, while increasing efficiency and price-performance ratio of photovoltaics.

The nano power cell can be used in a wide array of new energy applications based on the 3D solar cell technology. One example of the implementation of 3D photovoltaics (3D PV) is a disposable plug-in unit that can power personal electronics. These 3D PV units can also be connected into arrays that can power household appliances or serve as a mobile power source for outdoors. Further applications will include transparent 3D PV panels that can be put in windows and sky roofs to harvest solar power for household use. The 3D PVs production can be further scaled up. For example, flat spaces such as deserts can be staging areas for solar energy harvesting on a massive scale by employing 3D solar cell arrays that collect solar energy from multiple directions. In case flying sand and other debris adheres to these solar cell surfaces, the loss of the absorbed sunlight is minimized since the solar light is getting collected from the other faces of the array.

While the foregoing has been with reference to particular embodiments of the disclosure, it will be appreciated by those skilled in the art that changes in this embodiment may be made without departing from the principles and spirit of the disclosure, the scope of which is defined by the appended claims.

The invention claimed is:

1. A method for manufacturing electromagnetic radiation sensitive particles, the method comprising:
    embedding a plurality of particles into a barrier sheet;
    etching the barrier sheet to expose a top portion and a bottom portion of each particle embedded in the barrier sheet, wherein the exposed top portions of the particles are separated from the exposed bottom portions by the barrier sheet;
    attaching a metal material onto the exposed top portions; and
    attaching a dye material to the exposed bottom portions to create electromagnetic sensitive particles.

2. The method of claim 1 further comprising removing the barrier sheet once the metal material and dye material are attached to produce a plurality of electromagnetic sensitive particles.

3. The method of claim 1, wherein attached the metal material further comprising coating the exposed top portions.

4. The method of claim 3, wherein coating the exposed top portions further comprises depositing the metal material onto the exposed top portions.

* * * * *